United States Patent [19]

Kuehnle et al.

[11] Patent Number: 5,019,299
[45] Date of Patent: May 28, 1991

[54] PROCESS FOR THE MANUFACTURE OF WAX-LIKE ESTERIFICATION PRODUCTS

[75] Inventors: Adolf Kuehnle, Marl; Helmut Kehr, Schermbeck, both of Fed. Rep. of Germany

[73] Assignee: Chemische Werke Huels Aktiengesellschaft, Marl, Fed. Rep. of Germany

[21] Appl. No.: 534,010

[22] Filed: Jun. 6, 1990

Related U.S. Application Data

[63] Continuation of Ser. No. 283,029, Nov. 30, 1988, abandoned, which is a continuation of Ser. No. 204,961, Jun. 9, 1988, abandoned, which is a continuation of Ser. No. 90,415, Aug. 26, 1987, abandoned, which is a continuation of Ser. No. 759,571, Jul. 26, 1985, abandoned.

[30] Foreign Application Priority Data

Jul. 28, 1984 [DE] Fed. Rep. of Germany ....... 3427884

[51] Int. Cl.$^5$ ............................. C09F 5/08; C09F 7/10
[52] U.S. Cl. ................................................... 260/410.6
[58] Field of Search ...................................... 260/410.6

[56] References Cited

U.S. PATENT DOCUMENTS 4,029,682  6/1977  Foulks ............................. 260/410.6
4,185,094  1/1980  Crump .............................. 260/410.6

FOREIGN PATENT DOCUMENTS 1007398  3/1977  Canada ............................. 260/410.6
1274105  8/1968  Fed. Rep. of Germany .

OTHER PUBLICATIONS

Kohn, *Encyclopedia of Science and Technology*, vol. 14, pp. 508–510, McGraw-Hill.
Szabo et al., *Chemical Abstracts*, vol. 89, No. 91420p, 1978.
Translation of first page of German 1,274,105.

Primary Examiner—Bruce Gray
Attorney, Agent, or Firm—Millen, White & Zelano

[57] ABSTRACT

Wax-like esterification products derived from optionally partially saponified hard paraffin oxidation products and mono- or multivalent alcohols, which are suitable particularly as lubricants for plastics processing, are formed in the melt with particularly high degrees of esterification and without discolorization. The conversion is conducted at 160° to 220° C. in the presence of zinc salts such as zinc stearate.

21 Claims, No Drawings

PROCESS FOR THE MANUFACTURE OF WAX-LIKE ESTERIFICATION PRODUCTS

This application is a continuation of application Ser. No. 07/283,029, filed Nov. 30, 1988, which is a cont. of Ser. No. 07/204,961, of June 9, 1988, which is a cont. of Ser. No. 07/090,415 of Aug. 26, 1987, which is a cont. of Ser. No. 06/759,571 of July 26, 1985, all now abandoned.

CROSS-REFERENCE TO RELATED APPLICATIONS

This Application is related to commonly assigned, copending Application Ser. No. 759,573, now U.S. Pat. No. 4,661,163, of even date and which disclosure is incorporated entirely by reference herein.

BACKGROUND OF THE INVENTION

This invention relates to an improved esterification process for the oxidation products of synthetic hard paraffins.

It is a fact that esterification reactions have been the subject of substantial research. Thus, it is known to accelerate the esterification of lower fatty acids, which proceeds slowly in the absence of catalysts, by using mineral or Lewis acids. This involves a conversion of the poorly reacting cation which the nucleophilic oxygen atom of the alcohol enters into an addition with. This technique, however, becomes less effective as soon as higher fatty acids are involved, partly because of their lesser mobility, partly because the carboxyl function becomes less reactive.

On the other hand, in contrast to the esterification of lower fatty acids which with alkali form an undesirable stable carboxylate anion, the esterification of higher fatty acids with glycols can be accelerated by alkali hydroxide (Pardun, Seifen-Ole-Fett-Wachse 106, 65, 27 (1981)). Moreover, it is also known that various metal powders, oxides and salts can catalyze the esterification of fatty acids.

However, these processes cannot be applied to synthetic waxes, as has been stated in DE-AS 22 01 862 and DE-AS 24 32 215.

DE-AS 22 01 862 describes the esterification of polyethylene oxidation products with moro- or multivalent alcohols in the presence of sulphuric acid. According to its examples, however, no more than half of the waxy acids present in terms of the acid number can be esterified at 115° C.; at higher temperatures undesirable discolorations have to be expected. The desired complete esterification cannot, accordingly, be attained readily; as a result the specification refers to a low esterification readiness and long reaction periods. The need for a subsequent acid neutralization is also disadvantageous.

Consequently, there remains a need to provide a solution to this longstanding technical problem.

SUMMARY OF THE INVENTION

It is therefor an object of this invention to provide a high yield to complete esterification of the obtained oxidation products under mild conditions.

Upon further study of the specification and appended claims, further objects and advantages of this invention will become apparent to those skilled in the art.

These objects have been attained by this invention by providing a process for the preparation of waxy esterification products from hard paraffin oxidation products of synthetic origin, optionally partly saponified, on the one hand, and mono- or multivalent alcohols on the other hand, in the molten state, wherein the conversion is carried out in the presence of zinc compounds.

DETAILED DISCUSSION OF THE INVENTION

Suitable zinc compounds include, on the one hand, zinc oxide, zinc hydroxide and zinc mineral acid salts, e.g., the chloride, sulfate, nitrate, bromide , etc., and on the other hand, zinc salts of carboxylic acids, e.g., hydrocarbon aliphatic acids of 1–60 and above C-atoms, such as zinc stearate. The presence of the zinc ion is the important feature; the anion of the zinc compound must be compatible with the process of this invention. The zinc compound can be employed in catalytic amounts, e.g., of 0.01 to 3.0, preferably 0.5 to 2.0, in particular 0.1 to 1.0% by weight based on the amount of hard paraffin oxidation product employed.

Suitable hard paraffin oxidation products include Fischer-Tropsch oxidation products having a dropping point of 90° to 110° C. and polyethylene wax oxidation products having a dropping point of 95° to 140° C. Preferably, those products are used which are formed from molten hard paraffins by blowing with air at 120° to 250° C., in particular 130° to 180° C., preferably in the presence of a catalyst. This catalyst may in particular be a zinc salt, particularly a zinc soap such as zinc stearate or a so-called innoculant which itself is a hard paraffin oxidation product. The hard paraffins are oxidized to an acid number of 5 to 80, preferably 10 to 60; saponification numbers of such products are between 8 and 150, preferably from 16 to 120. Typical dropping points are 90°–140° C.

It is also possible to use partly saponified oxidation products for the esterification. The partial saponification is carried out either continuously during the oxidation or after completing the oxidation, by partly neutralizing the acid groups of the wax oxidation products in the molten state with bases such as sodium hydroxide, potassium hydroxide, lithium hydroxide, calcium hydroxide or zinc hydroxide or with mixtures of such bases.

Suitable hard paraffins which have been subjected to the required oxidation are synthetic hard paraffins manufactured according to the Fischer-Tropsch process, having a dropping point (DGF-M-III 3) between 100° and 120° C. and a molecular weight (determined by the vapor pressure technique osmometrically) of 600 to 800 as well as polyethylene hard paraffins. Those which are obtained by the known ethylene polymerization according to Ziegler either selectively or as a byproduct and have a molecular weight (determined by the vapor pressure technique osmometrically) of 1000 to 4000, preferably 1000 to 3000 are used preferably; such hard paraffins having a dropping point between 100° and 140° C. and a density between 0.91 and 0.97 g/cm$^3$. The nature of the wide scope of suitable oxidation products, their preparation, and the hard paraffin substrates from which they come are well known and discussed, e.g., in F. Ullmann, Encyklopadie der technischen Chemie, Band 24, 1–49 (1983), Verlag Chemie, Weinheim (Germany)

Suitable monovalent alcohols include aliphatic, preferably hydrocarbon and saturated alcohols having chain lengths (branched or straight chain) of 4 to 20 carbon atoms and terminal hydroxyl groups, preferably chain lengths of 6 to 12 carbon atoms. Suitable preferred bi-and higher valent alcohols (e.g., hydrocarbon aliphatic; saturated) include alcohols having 2 to 5 carbon atoms (branched or straight chain) and at least one terminal hydroxyl group, in particular, 1,2-ethanediol, 1,2-propanediol, 1,3-propanediol, 1,3-butanediol, 1,4-butanediol, glycerol and pentaerythritol. Mixtures of any of these alcohols can also be used.

Suitable alcohols are also well known to skilled workers; see, e.g., DE-OS 27 05 089.

The addition of alcohol is carried out using an amount from about half to twice the stoichiometric amount based on the acid number of the paraffin, preferably in amounts of 0 to 50% in excess of the amount stoichiometrically corresponding to the acid number. Where appropriate, excess alcohol is removed from the reaction mixture after the esterification by applying a vacuum.

The esterification can be conducted in an agitating vessel in a homogeneous mixture at normal pressure or at reduced pressure, e.g., 300-500 mm, at a temperature of 140° to 220° C., preferably 150°-200° C., in particular 160°-190° C. Typically, the esterification is finished after about 2-5 hours. The water formed during the reaction is removed in the form of steam by way of a distillation head and condensed in a condenser. If the esterification is carried out at reduced pressure, the distillation head and/or the cooler are not essential. Preferably the hard paraffin oxidation products, optionally partially saponified, are esterified completely, but at least to an extent of 70% of the waxy acids represented by the acid number of the original oxidized paraffin, resulting in a simultaneous drop of the acid number of the formed waxy esters to a level below 10 mg KOH/g.

An advantage of the new esterification method is that it is possible to operate safely above 160° C. without discoloration of the product so that the conversion proceeds relatively rapidly. Accordingly, for example, it is easy to lower the acid number of an oxidized polyethylene wax from an initial value of 65 during the esterification with ethylene glycol, within 5 hours, to below 10; the acid number is lowered by one-half even after less then 2 hours.

A further advantage is that the catalyst requires no neutralization, but may, in contrast to usual procedures, be left in the waxy ester. It is also possible to carry out the reaction in presence of a solvent (white spirit, e. g.).

A particular and surprising advantage is observed if for the esterification a hard paraffin oxidation product is employed which is of a type wherein a zinc soap had been used as a catalyst in its manufacture. In this case, the same catalyst, e.g., zinc stearate, may be used for both process stages, thus yielding an advantage which in chemistry is exceedingly rare.

The waxy esters obtained according to this invention, compared with the non-esterified hard paraffin oxidation products, are characterized by a higher polarity. For this reason they are particularly suitable, in combination with polar solvent systems, for the manufacture of finely dispersed wax dispersions. Because of their high compatibility with lacquer and printing die binders, they can be added to printing dies and lacquers for increasing resistance against abrasion or scratching without luster being substantially decreased. A preferred manner of application involves their use as a lubricant in the processing of thermoplastic resins, in particular PVC and in this context particularly treatment by rolling and calendaring in the manufacture of hard foils. This use is discussed in detail in commonly assigned, copending U.S. Pat. Application Ser. No. 759,573, now U.S. Pat. No. 4,661,163 filed on even date. This disclosure is incorporated by reference herein. Herein, acid number is determined conventionally, e.g., according to DGF-Einheitsmethoden M-IV 2.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Example 1

500 g of a polyethylene wax oxidation product (dropping point 103° C., penetration 4 mm $\times 10^{-1}$, acid number 25 mg KOH/g, saponification number 49 mg KOH/g, molecular weight (Mn) 1,900), 21 g of 1,2-ethanediol and 2.5 g of zinc stearate are introduced with stirring at a constant temperature of 130° C. into a 1000 ml three-necked flask fitted with a Claisen head and a Liebig condenser. The water of reaction separated in the condenser is collected in a receiving vessel. The progress of the reaction is controlled by way of acid number determinations. The reaction is completed after 3 hours. After removing the uncorrected ethanediol under a water vacuum, a wax is obtained which is almost white and has an acid number of 4 mg KOH/g. The product has a dropping point of 102° C and a penetration of 4 mm $\times 10^{-1}$.

Comparative Example 1

The procedure according to Example 1 is repeated except that no zinc stearate is added. In this case the acid number after 3 hours is still as high as 13 mg KOH/g. Even though the reaction is continued for a further 3 hours, the acid number does not drop below 7 mg KOH/g.

Example 2

The same procedure is followed as in Example 1, but using a polyethylene wax oxidation product (dropping point 107° C., penetration 2 mm $10^{-1}$, acid number 24 mg KOH/g, saponification number 43 mg KOH/G, molecular weight (Mn) 1300) which already contains 0.5 weight % of zinc stearate as the oxidation catalyst. No additional zinc stearate is added. Even after 2 hours, the acid number has dropped to 6 mg KOH/g. After 3.5 hours the reaction is completed. An almost white wax having an acid number of 3 mg KOH/g is obtained.

Example 3

800 g of a polyethylene wax oxidation product (dropping point 104° C., penetration 4 mm $\times 10^{-1}$, acid number 63 mg KOH/g, saponification number 112 mg KOH/g) which already contains 0.5 weight % zinc stearate as an oxidation catalyst, is stirred jointly with 83 g of 1,2-ethanediol at a constant temperature of 180° C. into a 2000 ml three-neck flask fitted with a Claisen head and a Leibig condenser. The progress of the reaction is monitored with reference to acid number determinations. Even after 2 hours, the acid number has dropped by 41 units to 22 mg KOH/g. After 5 hours the reaction is terminated at an acid number of 7 mg KOH/g and non-converted ethanediol is removed under water jet vacuum. An almost white wax is obtained having a dropping point of 103° C. and a penetration of 4 mm×10⁻¹.

Example 4

The procedure as in Example 3 is followed but by converting 1000 g polyethylene wax oxidation product with 1.0 g of 1,4-butanediol. Even after 2 hours the acid number has dropped by half to 28 g KOH/g. After 6 hours the reaction is terminated at an acid number of 8 mg KOH/g.

Example 5

The same procedure as in Example 3 is followed, but by converting 800 g of polyethylene wax oxidation product with 85 g of glycerine. After 2 hours the acid number has dropped by half to 30 mg KOH/g. After 7 hours the reaction is terminated at an acid number of 9 mg KOH/g.

Example 6

The same procedure is followed as in Example 3 except that 800 g of polyethylene wax oxidation product is converted with 123 g of pentaerythritol. After 7 hours the reaction is terminated at an acid number of 9 mg KOH/g.

Example 7

1000 g of a polyethylene wax oxidation product partly saponified (15 acid units) with lithium hydroxide and calcium hydroxide (dropping point 104° C., penetration number 1 mm×10⁻¹, acid number 25 mg KOH/g, saponification number 51 mg KOH/g, molecular weight (Mn) 1400), already containing 0.5% by weight zinc stearate as an oxidation catalyst is esterified with 28 g of 1,2-ethanediol at a temperature of 180° C. After 3 hours the reaction is terminated at an acid number of 6 mg KOH/g.

Example 8

1000 g of a Fischer-Tropsch oxidation product (dropping point 101° C., penetration 5 mm×10⁻¹, acid number 30 mg KOH/g, saponification number 55 mg KOH/g, molecular weight (Mn) 600) is esterified at 180° C. in a 2000 ml three-neck flask—analogous to Example 1—with 53 g of 1,2-ethanediol and an addition of 5 g of zinc stearate. After as little as 1 hour, 80% of the acid groups have been esterified and after a further hour the acid number has dropped to 3. An almost white product having a dripping point of 101° C. and penetration of 5 mm×10⁻¹ is obtained.

Comparative Example 2

The same procedure is followed as in Example 8 but without the use of zinc stearate. In this case the acid number after 1 hour is still as high as 22 mg KOH/g. After 7 hours the reaction is stopped at an acid number of 12 mg KOH/g.

Example 9

The same procedure is adopted as in Example 8 but using 1 g of zinc chloride instead of zinc stearate. After 2 hours an acid number of 8 mg KOH/g is attained. After 2 further hours a producing having an acid number of 4 mg KOH/g is isolated.

Example 10

The same procedure is employed as in Example 8 but using 2 g of zinc hydroxide instead of zinc stearate. In this case the acid number has dropped to a value of 4 mg KOH/g after as little as 2 hours. After a further hour the reaction is terminated at an acid number of 2 mg KOH/g.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of waxy esterification products comprising reacting acidic, hard paraffin oxidation products of synthetic origin with an alcohol in the molten state in the presence of an effective amount of a catalytic zinc compound.

2. A process of claim 1, wherein the hard paraffin oxidation product has been partially saponified prior to reaction with the alcohol.

3. A process of claim 1, wherein at least 70% of the acid function of the paraffin oxidation products as determined by acid number is esterified, and wherein the acid number of the waxy ester product is lowered to a value below 10 mg KOH/g.

4. A process of claim 1, wherein the zinc compound is an oxide, a hydroxide or a mineral acid salt.

5. A process of claim 1, wherein the zinc compound is the zinc salt of a carboxylic acid.

6. A process of claim 1, wherein the hard paraffin oxidation product is an air oxidized product of a Fischer-Tropsch synthesis or an oxidized product of an ethylene polymerization by the Ziegler process.

7. A process of claim 6, wherein the hard paraffin oxidation product has an acid number of 5 to 80 and was prepared in molten condition in the presence of a zinc salt by air oxidation of a product of ethylene polymerization by the Ziegler process having a molecular weight (determined by the vapor pressure technique osmometrically) of 1000 to 4000.

8. A process of claim 1, wherein the amount of zinc compound is 0.01 to 3.0 weight %.

9. A process of claim 1, wherein the zinc compound is zinc stearate.

10. A process of claim 1, wherein the alcohol is a monovalent alcohol of 4-20 carbon atoms having a terminal hydroxy group.

11. A process of claim 1, wherein the alcohol is multivalent.

12. A process of claim 11, wherein the alcohol is of 2-5 C-atoms and has at least one terminal OH group.

13. A process of claim 1, wherein the alcohol is 1,2-ethanediol, 1,2-propanediol, 1,3-propanediol, 1,3-butanediol, 1,4-butanediol, glycerine or pentaerythritol.

14. A process of claim 1, wherein the amount of alcohol is from 1 to 1.5 times the stoichiometric amount.

15. A process of claim 4, carried out at a temperature of 140°–220° C.

16. A process of claim 1, wherein the hard paraffin oxidation product was prepared using a zinc catalyst and the same zinc catalyst is used as said catalytic zinc compound.

17. A waxy esterification product prepared by the process of claim 1.

18. A waxy esterification product prepared by the process of claim 3.

19. A waxy esterification product prepared by the process of claim 9.

20. A process of claim 1 wherein the paraffin oxidation product has a dropping point of 90°-110° C. and is prepared by Fischer-Tropsch oxidation or has a dropping point of 95° to 140° C. and is a polyethylene wax oxidation product.

21. A process of claim 1 wherein the paraffin oxidation prooduct has a dropping point of 90°-140° C.

* * * * *